(12) United States Patent
Laukkanen et al.

(10) Patent No.: US 8,159,353 B2
(45) Date of Patent: Apr. 17, 2012

(54) PORTABLE ELECTRONIC DEVICE, METHOD, AND COMPUTER-READABLE MEDIUM FOR DETERMINING USER'S ACTIVITY LEVEL

(75) Inventors: Raija Laukkanen, Espoo (FI); Eeva Kiuru, Oulu (FI)

(73) Assignee: Polar Electro Oy, Kempele (FI)

( * ) Notice: Subject to any disclaimer, the term of this patent is extended or adjusted under 35 U.S.C. 154(b) by 433 days.

(21) Appl. No.: 11/958,879

(22) Filed: Dec. 18, 2007

(65) Prior Publication Data
US 2008/0150731 A1 Jun. 26, 2008

(30) Foreign Application Priority Data
Dec. 20, 2006 (FI) .................................... 20065828

(51) Int. Cl.
*G08B 23/00* (2006.01)
(52) U.S. Cl. ................. 340/573.1; 340/604; 340/605; 600/300; 600/595; 128/903; 128/920
(58) Field of Classification Search ............... 340/573.1, 340/604, 605; 600/300, 595, 513, 519; 128/903, 128/920; 455/414.1
See application file for complete search history.

(56) References Cited

U.S. PATENT DOCUMENTS

| | | | | |
|---|---|---|---|---|
| 5,928,189 A * | 7/1999 | Phillips et al. | ................. | 604/65 |
| 6,721,706 B1 * | 4/2004 | Strubbe et al. | ................. | 704/275 |
| 6,731,307 B1 * | 5/2004 | Strubbe et al. | ................. | 715/727 |
| 7,091,865 B2 * | 8/2006 | Cuddihy et al. | ........... | 340/573.1 |
| 7,095,328 B1 * | 8/2006 | Stern et al. | ................. | 340/573.1 |
| 7,220,220 B2 * | 5/2007 | Stubbs et al. | .................. | 482/72 |
| 7,522,057 B2 * | 4/2009 | Stern et al. | ................. | 340/573.1 |
| 7,586,418 B2 * | 9/2009 | Cuddihy et al. | ........... | 340/573.1 |
| 7,676,262 B1 * | 3/2010 | Xi et al. | ........................ | 600/519 |
| 7,728,723 B2 | 6/2010 | Niva et al. | | |
| 2001/0004234 A1 * | 6/2001 | Petelenz et al. | ............... | 340/539 |
| 2002/0118121 A1 | 8/2002 | Lehrman et al. | | |
| 2005/0065560 A1 * | 3/2005 | Lee et al. | ......................... | 607/6 |
| 2005/0099492 A1 * | 5/2005 | Orr | ........................ | 348/14.08 |
| 2005/0171410 A1 * | 8/2005 | Hjelt et al. | ..................... | 600/300 |
| 2005/0172311 A1 * | 8/2005 | Hjelt et al. | ..................... | 725/10 |
| 2005/0181771 A1 * | 8/2005 | Cuddihy et al. | ........... | 455/414.1 |
| 2005/0230596 A1 * | 10/2005 | Howell et al. | ................ | 250/200 |
| 2005/0245839 A1 * | 11/2005 | Stivoric et al. | ................ | 600/549 |
| 2005/0248718 A1 * | 11/2005 | Howell et al. | ................. | 351/41 |
| 2006/0020295 A1 * | 1/2006 | Brockway et al. | .............. | 607/17 |

(Continued)

FOREIGN PATENT DOCUMENTS
EP 1849504 B1 11/2008
(Continued)

OTHER PUBLICATIONS

Levine et al., "Interindividual Variation in Posture Allocation: Possible Role in Human Obesity", Science, vol. 307, pp. 584-586 (2005).

(Continued)

*Primary Examiner* — Hoi Lau
(74) *Attorney, Agent, or Firm* — Hoffmann & Baron, LLP (57) ABSTRACT

The invention relates to a portable electronic device, a method, and a computer software product. The portable electronic device comprises an active time unit for determining a user activity level during a predetermined period of time; and a processing unit for determining a user inactivity level during a predetermined period of time on the basis of the determined activity level.

30 Claims, 4 Drawing Sheets

U.S. PATENT DOCUMENTS

| | | | |
|---|---|---|---|
| 2006/0020421 A1* | 1/2006 | Darley et al. | 702/182 |
| 2006/0052727 A1 | 3/2006 | Palestrant | |
| 2006/0066448 A1* | 3/2006 | Berisford et al. | 340/504 |
| 2006/0089538 A1* | 4/2006 | Cuddihy et al. | 600/300 |
| 2006/0139166 A1* | 6/2006 | Choutier et al. | 340/539.12 |
| 2006/0161070 A1* | 7/2006 | Siejko et al. | 600/528 |
| 2006/0255955 A1 | 11/2006 | O'Connor et al. | |
| 2007/0061105 A1* | 3/2007 | Darley et al. | 702/182 |
| 2007/0069900 A1* | 3/2007 | Stern et al. | 340/573.1 |
| 2007/0073178 A1* | 3/2007 | Browning et al. | 600/519 |
| 2007/0129622 A1* | 6/2007 | Bourget et al. | 600/382 |
| 2007/0129769 A1* | 6/2007 | Bourget et al. | 607/45 |
| 2007/0167850 A1* | 7/2007 | Russell et al. | 600/513 |
| 2008/0001735 A1* | 1/2008 | Tran | 340/539.22 |
| 2008/0084296 A1* | 4/2008 | Kutzik et al. | 340/540 |
| 2008/0117060 A1* | 5/2008 | Cuddihy et al. | 340/573.1 |
| 2008/0133742 A1* | 6/2008 | Southiere et al. | 709/224 |
| 2009/0048540 A1* | 2/2009 | Otto et al. | 600/595 |
| 2009/0069724 A1* | 3/2009 | Otto et al. | 600/595 |
| 2009/0069787 A1* | 3/2009 | Estes et al. | 604/503 |
| 2009/0121863 A1* | 5/2009 | Prior | 340/539.12 |
| 2009/0212941 A1* | 8/2009 | Vock et al. | 340/539.32 |
| 2009/0260426 A1* | 10/2009 | Lieberman et al. | 73/65.01 |

FOREIGN PATENT DOCUMENTS

| | | |
|---|---|---|
| FI | 119619 B | 10/2007 |
| WO | W002061705 A1 | 8/2002 |
| WO | W02005070289 A1 | 8/2005 |

OTHER PUBLICATIONS

Finnish Official Action issued in the Finnish priority Application No. 20065828.

* cited by examiner

PORTABLE ELECTRONIC DEVICE, METHOD, AND COMPUTER-READABLE MEDIUM FOR DETERMINING USER'S ACTIVITY LEVEL

CROSS-REFERENCE TO RELATED APPLICATION

This application claims priority based on Finnish patent application No. 20065828, filed Dec. 20, 2006, which is incorporated herein by reference.

BACKGROUND OF THE INVENTION

1. Field of the Invention

The invention relates to a portable electronic device, a method, and a computer software product.

2. Description of the Related Art

A day may be divided into three main parts: rest (sleep), work, and leisure time. The periods of time spent for leisure and work are mainly determined by external factors. The way each one of us spends his or her leisure time may be determined individually, and this may also be influenced e.g. in an activating manner. Various environmental factors, such as television, DVD, the Internet, and games, greatly add to an inactive manner of spending one's leisure time.

It is a well known fact that too much physical inactivity, such as sitting and immobility, increase health problems. Inactivity results in poor condition, increased body weight, and metabolic problems which, in turn, increase risks of several different diseases, such as obesity, coronary artery disease, type 2 diabetes, hypertension as well as disorders relating to muscles and bones. In physical inactivity, sitting equals lying, since both requires minimum muscular activity and both thus consume very little energy and present a metabolic need. According to recent research, the most significant difference between slim persons and obese persons is that overweight persons sit on average two hours longer than slim ones. For example, Levine et al., "Interindividual Variation in Posture Allocation: Possible Role in Human Obesity", Science, January 2005, Vol. 307, p. 584 to 586, discloses that controlling the amount of time spent by an individual sitting may have a considerable effect on weight and health management as well as on the individual's desire to achieve a more active lifestyle.

For instance, the work of a typical office worker contains hardly any physical activity and, further, such a person daily spends sitting: 6 to 7 hours in the office, a total of 1 hour in the car commuting, and 3 hours while watching television. The only activity of a typical workday is e.g. a forty-minute walk before dinner. Thus, a total of time spent sitting per workday is no less than 11 to 12 hours, which considerably exceeds the recommended healthy amount.

An inactive non-workday (e.g. reading, working on a computer, minor domestic chores, watching television) contains 8 to 9 hours of sitting and only 3 hours of activity. Hence, the time spent inactively exceeds the recommended amounts. An active non-workday (e.g. golfing, shopping) may contain 5 to 6 hours of sitting as well as an equal amount of activity. Consequently, the time spent inactively remains at a recommended level, i.e. below 7 hours.

The time spent inactively by a typical user may be e.g. 74 hours per week. This amount is well above the recommended weekly maximum inactivity values. All in all, it may be stated that more often than not, the amount of time spent inactively, such as sitting, on workdays should be diminished in order to maintain a slim build and health.

People do not easily notice the amount of inactivity in their daily life. Therefore, increasing the awareness of the amount of inactivity in an individual's daily life may be even more significant for health than monitoring the activity of the individual. Various devices for monitoring physical condition do not meet these needs.

SUMMARY OF THE INVENTION

An object of the invention is to provide a method and an apparatus implementing the method so as to enable the amount of inactivity to be estimated. As a first feature of the invention there is presented a portable electronic device comprising: an active time unit for determining a user activity level during a predetermined period of time; and a processing unit for determining a user inactivity level during a predetermined period of time on the basis of the determined activity level.

As a second feature of the invention there is presented a method comprising: determining a user activity level during a predetermined period of time on the basis of a portable electronic device used by the user; and determining a user inactivity level on the basis of the determined activity level.

As a third feature of the invention there is presented a computer software product comprising encoded instructions for executing a computer process in a digital processor. The computer process comprises: determining a user activity level during a predetermined period of time on the basis of data produced by a portable electronic device used by the user; and determining a user inactivity level during a predetermined period of time on the basis of the determined activity level.

The invention is based on the invention comprising determining an inactivity level during a predetermined period of time on the basis of the determined activity level.

Several advantages are achieved by the method and system according to the invention. As an advantage, the invention produces an objective estimation of user inactivity. It becomes possible to monitor a person's inactivity level e.g. on a daily, weekly, and/or monthly basis. Furthermore, it becomes easier to maintain the amount of personal activity within limits advantageous to health.

BRIEF DESCRIPTION OF THE DRAWINGS

The invention is now described in closer detail in connection with preferred embodiments and with reference to the accompanying drawings, in which.

DETAILED DESCRIPTION OF THE PREFERRED EMBODIMENTS

Figure 1:
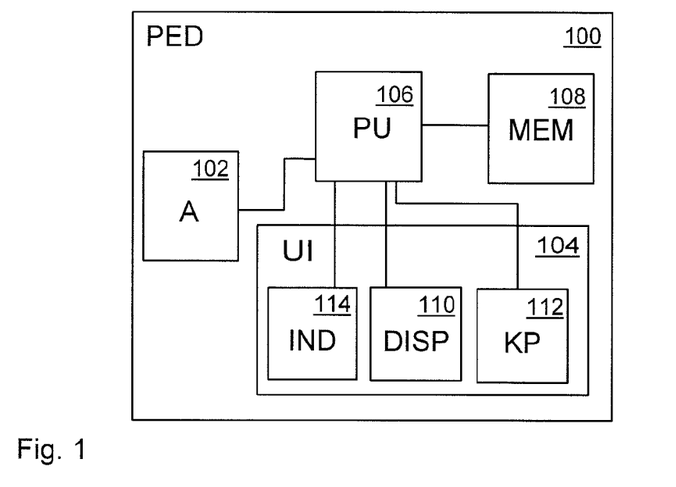
FIG. 1 shows an example of a structure of a portable electronic device.

Referring to the example of FIG. 1, a portable electronic device (PED) 100 comprises a processing unit (PU) 106 and a memory unit (MEM) 108. The processing unit 106 comprises a digital processor and executes a computer process in accordance with encoded instructions stored in the memory unit 108.

The processing unit 106 may be implemented using analog circuits, ASICs (Application Specific Integrated Circuit), digital processor, memory, and computer software. The processing unit 106 may constitute a part of the computer of the device 100. The processing unit 106 may execute a computer process in accordance with encoded instructions stored in the memory unit 108.

The portable electronic device 100 is e.g. a mobile telephone or a pedometer. In an embodiment, the portable electronic device 100 is a wrist device, which may be e.g. a wrist device 202 shown in FIG. 2. In addition to the wrist device 202, the device 100 may comprise one or more auxiliary devices 204, 206, such as a motion sensor 206 to be attached to a limb of the user 200 of the portable electronic device and/or a heart rate transmitter 204 indicating electric pulses induced by the heart. Such an auxiliary device 204, 206 may communicate wiredly or wirelessly with the wrist device 202. In this connection, a user 200 of the portable electronic device is called a user 200.

Figure 2:
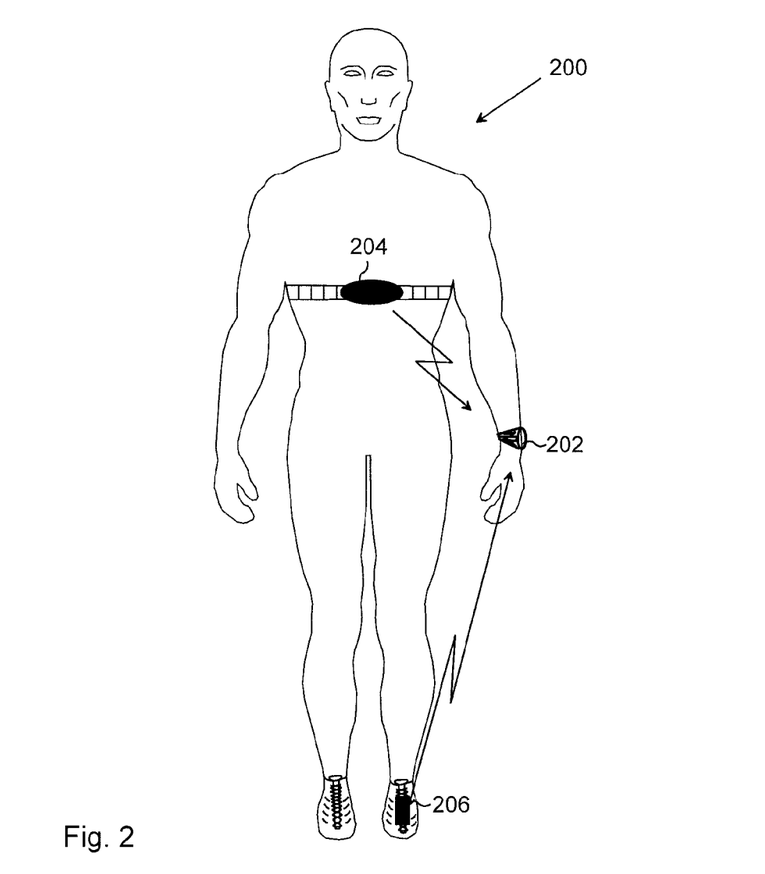
FIG. 2 shows a second example of a structure of a portable electronic device.

In an embodiment, the portable electronic device 100 comprises a wrist device 202 and at least one auxiliary device 204, 206. Instead of the wrist, the portable electronic device 100 may be freely placed also in other parts of the body, and e.g. in a pocket, on a piece of clothing, footwear or accessories.

Still referring to FIG. 1, the portable electronic device 100 further comprises an active time unit (A) 102 for determining a user activity level during a predetermined period of time. In an embodiment, the active time unit 102 comprises one or more motion detectors to generate motion data characterizing a local movement of the portable electronic device 100 for determining an activity level.

In an embodiment, the active time unit 102 is located in a wrist device 202.

In an embodiment, the active time unit 102 is located in an auxiliary device 204, 206.

Typically, a local movement of the portable electronic device 100 comprises movements of a limb or another part of the body of the user 200, which includes a motion component associated with the user's 200 stepping. The amplitude of such local movements is typically of the order of magnitude of the amplitude of movements of the user's 200 limbs.

In an embodiment, the active time unit 102 comprises an acceleration sensor, which measures acceleration associated with the user's 200 movement. The acceleration sensor converts acceleration induced by motion or a gravitational force into an electric signal.

In an embodiment, the acceleration sensor is based on piezo-resistor technology using a material whose resistance changes when a piezo-resistor is compressed as a result of acceleration of mass. When a constant current is applied through the piezo-resistor, a voltage acting over the piezo-resistor changes according to the compression induced by the acceleration.

In an embodiment, the acceleration sensor is based on piezo-electric technology, wherein a piezo-electric sensor generates a charge upon accelerating the acceleration sensor. In silicon bridge technology, a silicon chip is etched such that a silicon mass is left on the silicon chip at an end of a silicon beam. When the silicon chip is subjected to acceleration, the silicon mass directs a force to the silicon beam, whereby the resistance of the silicon beam changes.

The acceleration sensor may also be based on micro-machined silicon technology, which is based on using a differential capacitor. The acceleration sensor may also be based on voice coil technology, which is based on the same principle as a microphone. Some examples of suitable motion sensors include: Analog Devices ADXL105, Pewatron HW or VTI Technologies SCA-series.

The acceleration sensor may also be based on other appropriate technologies, e.g. a gyroscope integrated in a silicon chip, a micro vibration switch arranged in a surface-mountable component or a mechanical pendulum.

Motion data generated by the acceleration sensor may be conveyed to a central processing unit 106 or a memory unit 108. The motion data may comprise e.g. acceleration data and/or motion pulse data associated with the user's 200 movements.

The active time unit 102 may also be implemented by other appropriate technologies, e.g. a gyroscope integrated in a silicon chip or a micro vibration switch arranged in a surface-mountable component.

The active time unit 102 may comprise a pre-processing unit for processing primary motion data, such as acceleration data and/or vibration data. The processing may comprise converting the primary motion data into secondary motion data, such as changing acceleration data associated with the movements generated by the user into motion pulse data. The processing may also comprise filtering the primary and/or secondary motion data.

The portable electronic device 100 may further comprise a user interface (UI) 104, which typically includes a display unit (DISP) 110 and a display controller. The display unit 110 may include e.g. LCD (Liquid Crystal Display) components. The display unit 110 may, graphically and/or digitally, display to the user 200 e.g. an instantaneous activity level and inactivity level during a predetermined period of time.

The user interface 104 may also comprise a keypad (KP) 112 to enable the user 200 to enter commands into the device 100. The user interface 102 may also include an indicator 114 to enable the device to impart voice signals, vibration-based signals and/or light-based signals.

In an embodiment, the wrist device 202 is a heart rate monitor, in which case the heart rate monitor may comprise a receiver for receiving a signal transmitted from a heart rate measurement unit. The heart rate measurement unit may be a belt-like construction to be mounted on the user's chest, comprising means for carrying out electrocardiography (ECG) and transmitting ECG data to the wrist device 202.

In an embodiment, the active time unit 102 determines a user activity level during a predetermined period of time, and the processing unit 106 determines a user inactivity level during a predetermined period of time on the basis of the activity level determined in the active time unit 102.

In an embodiment, the active time unit 102 is configured to add up periods of time during which an instantaneous motion intensity value meets predetermined activity conditions.

In an embodiment, the active time unit 102 comprises at least one activity sensor for measuring a user activity level, and the processing unit 106 is configured to use the measured activity level in determining an inactivity level.

In an embodiment, at least one activity sensor is configured to measure muscular activity of a user, in which case the processing unit 106 may determine an inactivity level during a particular period of time on the basis of the measured muscular activity.

In an embodiment, at least one activity sensor is configured to measure heart rate of a user, in which case the processing unit 106 may determine an inactivity level during a particular period of time on the basis of the measured heart rate pulses.

For instance, an inactivity level during a particular period of time may be determined on the basis of variations in a personal heart rate.

In an embodiment, the active time unit 102 comprises at least one acceleration sensor for measuring acceleration from movement of the device when the user is moving, and the processing unit 106 is configured to use the measured acceleration in determining an inactivity level.

Thus, measurement results describing the movement, muscular activity, and/or heart rate of the user or combinations thereof may be used in determining the inactivity level.

In an embodiment, the processing unit 106 is configured to detect reaching at least one predetermined threshold value in the determined inactivity level. In an embodiment, the predetermined threshold value is an optimal inactivity level during a predetermined period of time. In an embodiment, the determined threshold value is a maximum inactivity level during a predetermined period of time. The optimal inactivity level is e.g. an optimal level of inactivity allowed during a day which is not advisable to be exceeded. The maximum inactivity level is e.g. a maximum level of inactivity allowed during some hours or during a day, exceeding which is to be avoided.

In an embodiment, the indicator 110, 114 indicates the determined inactivity level. In an embodiment, the indicator 110, 114 is configured to indicate reaching at least one predetermined threshold level in the inactivity level. The indicator may indicate e.g. reaching/exceeding the optimal inactivity level and/or reaching/exceeding the maximum inactivity level.

Figure 3:
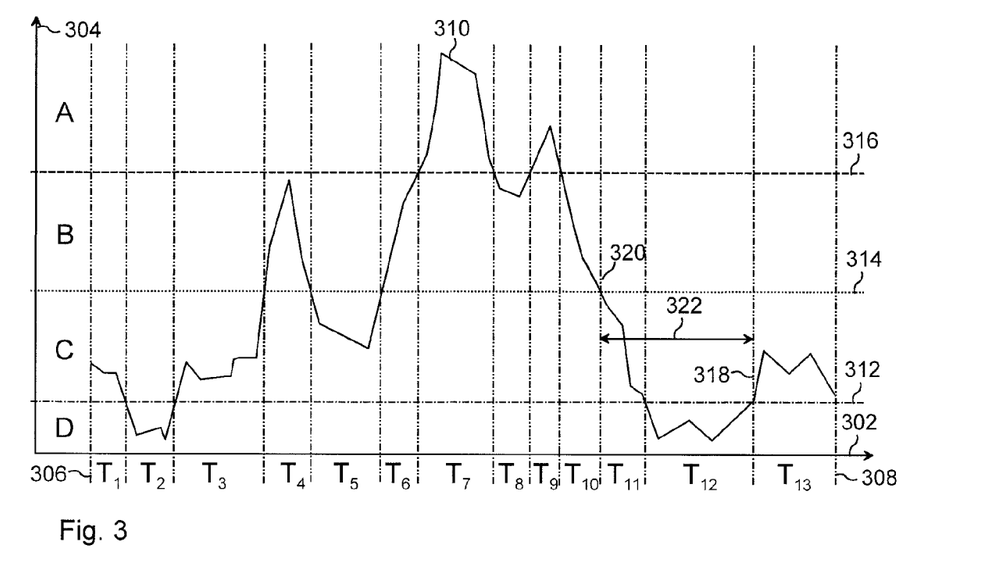
FIG. 3 shows an example of a motion intensity curve.

Referring to the example of FIG. 3, let us examine a motion intensity curve 310 showing a time dependency of an instantaneous motion intensity value of the user 200. A horizontal axis 302 shows time expressed in a time unit, such as minute, while a vertical axis 304 shows a motion intensity value expressed in a motion intensity unit, such as pulse/minute (p/min).

The motion intensity value characterizes the amount of movement of the user 200 in a time unit. In an embodiment, the motion intensity value characterizes the number of motion pulses per minute or another appropriate time unit. The activity level may be determined e.g. on the basis of the number of motion pulses.

An instantaneous motion intensity value is a motion intensity value calculated for a point of time. An instantaneous motion intensity value at a point of time may be determined e.g. by calculating motion pulses accumulated during a measurement time period, such as a minute, and dividing the number of motion pulses by the measurement time period. A point of time to be associated with the determined instantaneous motion intensity value may be e.g. a starting time or an end time of a measurement time period or a point of time halfway the measurement time period.

An active time accumulation is an accumulating time accumulation which includes, added up, periods of time during which the instantaneous motion intensity value meets predetermined activity criteria. In the example of FIG. 3, a predetermined activity criterion is e.g. a motion intensity level 314 designated in dotted line, time periods meeting the activity criteria then being T4, T6, T7, T8, T9, and T10. Thus, in determining the activity level, the user's very slight movement, for example, is not necessarily counted as activity.

In an embodiment, the activity level is determined on the basis of an active time accumulation calculated for a previously known period of time which, in the example of the figure, may be a period of time between a starting time 306 and an end time 308. In such a case, the active time accumulation for the particular period of time is T4+T6+T7+T8+T9+T10 when the pre-determined activity criterion is the motion intensity level 314. The periods or time may be implemented such that the periods overlap with one another. For instance, let us examine 60-second time periods at intervals of e.g. ten seconds. Then, to the 60-second time period are added at intervals of ten seconds instantaneous motion intensity values for the most recent ten seconds while simultaneously omitting motion intensity values for the least recent ten seconds.

The starting time 306 may be 12 o'clock at night or a point of time 24 hours preceding real time. The end time 308 may be 12 o'clock at night without, however, limiting the disclosed solution to the presented embodiment.

When the active time determination is in operation, the end time 308 may be a point of time in real time. In such a case, the active time accumulation indicates an active time accumulation accumulated from the starting time 306 to the point of time in real time.

In an embodiment, the inactivity level is determined from an inactive time accumulation which includes, added up, periods of time during which the instantaneous motion intensity value meets predetermined inactivity criteria. A predetermined inactivity criterion is e.g. a predetermined motion intensity level which determines an upper limit of the instantaneous motion intensity value. The inactive time accumulation may be shown to the user by means of the display unit 110.

In the example of FIG. 3, the predetermined inactivity criterion is e.g. a motion intensity level 314 designated in dotted line, time periods meeting the inactivity criteria then being T1, T2, T3, T5, T11, T12, and T13. The inactive time accumulation for the period of time between the starting time 306 and the end time 308 is thus T1+T2+T3+T5+T11+T12+T13.

In an embodiment, the portable electronic device 100 divides the instantaneous motion intensity values into at least two activity categories based on predetermined threshold values and the active time accumulation is determined activity-category-specifically. The example of FIG. 3 shows activity categories A, B, and C. Activity category C comprises motion intensity values residing between the motion intensity levels 312 and 314, activity category B comprises motion intensity values residing between the motion intensity levels 314 and 316, and activity category A comprises motion intensity values residing above the motion intensity level 316.

Activity category D comprises motion intensity values residing below the motion intensity level 312, and activity category D may also be defined as an inactivity category.

The motion intensity levels 312, 314, and 316 may be 2 p/min, 30 p/min, and 50 p/min, in the given order. Thus, activity category D may be defined as rest, activity category C may be defined as an extremely light activity category, activity category B may be defined as a light activity category, and activity category A may be defined as a moderate/heavy activity category.

In the shown example, the category-specific active time accumulations are as follows:

Intensity category A: T7+T9
Intensity category B: T4+T6+T8+T10
In this case, the inactive time accumulation is T1+T2+T3+T5+T11+T12+T13.

Figure 4:
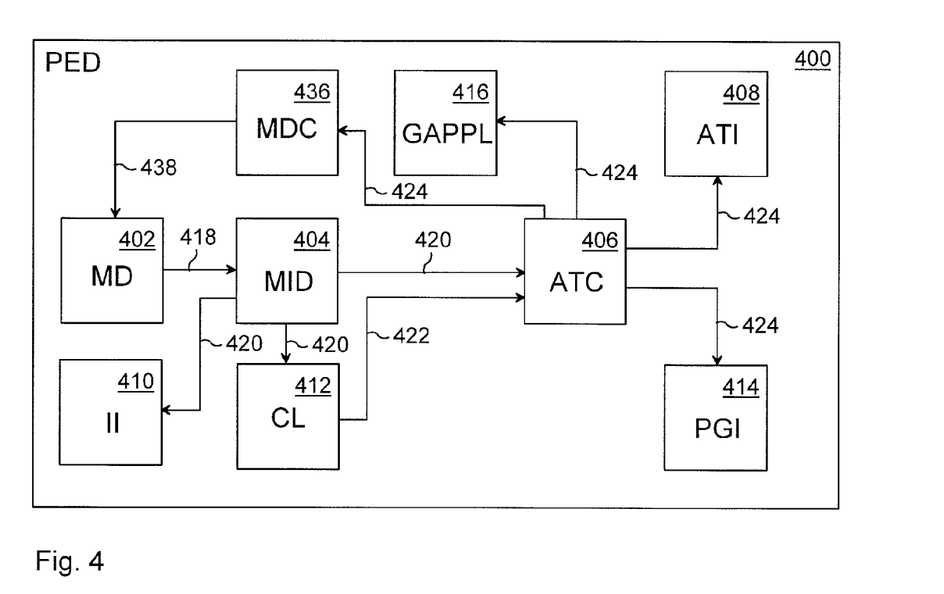
FIG. 4 shows an example of a structure of a portable electronic device.

Referring to the example of FIG. 4, let us examine a portable electronic device (PED) 400 comprising a motion detector (MD) 402, a motion intensity determinator (MID) 404, and an active time calculator (ATC) 406.

The motion detector 402 generates motion data 418 characterizing a local movement of the portable electronic device 400 and feeds the motion data 418 to the motion intensity determinator 404. The motion intensity determinator 404 determines instantaneous motion intensity values 420 from the motion data 418.

In an embodiment, the motion intensity determinator 404 filters motion data 422 on the basis of predetermined time characteristics. The motion intensity determinator 404 may accept motion pulses meeting the pre-determined criteria and use the accepted motion pulses for determining motion intensity values.

In an embodiment, in determining a motion intensity value, the motion intensity determinator 404 uses motion pulses whose length of time intervals therebetween resides within predetermined limits. In such a case, the determination of the motion intensity values concentrates on motion frequencies typical of a human body, typically being 1 to 2 pulses per second. The filtering may be implemented by rejecting successive motion pulses whose time interval is below a predetermined lower limit or whose time interval is above a predetermined upper limit.

The predetermined upper and lower limits may depend on the location of the motion detector 402 on the user's body. In the case of a motion detector 402 attached to an upper limb, the predetermined lower limit may be e.g. 0.4 seconds. The predetermined upper limit may be e.g. 2.0 seconds.

The motion intensity determinator 404 may be implemented by means of a computer process to be executed in the central processing unit 106, the computer process being encoded in encoded instructions to be stored in the memory unit 108.

In an embodiment, the motion intensity determinator 404 feeds the instantaneous motion intensity values 420 to the active time calculator 406. The motion intensity determinator 404 may also feed a point of time associated with each instantaneous motion intensity to the active time calculator. The active time calculator 406 compares the motion intensity values with the predetermined motion intensity level 314 and calculates the active time accumulation and possibly the inactive time accumulation on the basis of the comparison. Inactive time accumulation data may be incorporated in active time accumulation data 424.

In an embodiment, the portable electronic device 400 comprises a classifier (CL) 412 which receives the motion intensity values 420 from the motion intensity determinator 404 and carries out a comparison between the motion intensity values 420 and the motion intensity levels 312, 314, 316. On account of the comparison, the classifier 412 divides the instantaneous motion intensity values into intensity classes.

The active time calculator 406 may be implemented by means of a computer process to be executed in the central processing unit 106, the computer process being encoded in encoded instructions to be stored in the memory unit 108. The classifier 412 may be implemented by means of a computer process to be executed in the central processing unit 106, the computer process being encoded in encoded instructions to be stored in the memory unit 108. The inactive time accumulation may be shown to the user 200 by means of the display unit 110.

In an embodiment, the portable electronic device 400 comprises an indicator (ATI) 408 for indicating the inactive time accumulation and/or active time accumulation preceding the period of time between the starting time 306 and the end time 308 to the user. The inactive and active time accumulations of previous, e.g. day-specific, time periods may be stored in the memory unit 108 and shown to the user 200 by means of the display unit 110 graphically or digitally. This enables the user 200 to monitor his or her performance history and compare e.g. the inactive time accumulation of the ongoing time period with previous values.

In an embodiment, the portable electric device 400 comprises an intensity indicator (II) 410 for indicating the point of time of the most recent motion intensity value meeting the activity criteria to the user 200. Referring to FIG. 3, let us assume that the real time moment is a point of time 318, and the activity criterion is determined by the motion intensity level 314. In such a case, the most recent point of time of the motion intensity value meeting the activity criteria with respect to the point of time 318 is a point of time 320. The central processing unit 106 may feed the most recent point of time of the motion intensity value meeting the activity criteria to the memory unit 108 to be stored therein. The display unit 110 may indicate the memory space of the memory unit 108 such that the contents of the memory are shown on the display unit 110. By detecting the most recent point of time of the motion intensity value meeting the activity criteria the user 200 may conclude e.g. the length of ongoing inactive time 322. The display unit may e.g. show the text "inactive since T1:T2", wherein T1:T2 is the point of time at which the activity criterion was met last.

In an embodiment, the portable electric device 400 may generate a performance instruction on the basis of an inactive time accumulation.

The active time calculator 406 feeds active time accumulation data 424 to a performance instruction generator 414, which may compare the active time accumulation with reference values. The reference values may form ranges which are associated with performance instructions. A performance instruction may include an instruction REST, WALK, and LIGHT EXERCISE. For instance, if the accumulation for the present day or previous 24 hours in activity categories A and B is less than 30 minutes, the user may be given a performance instruction to increase his or her activity e.g. by exercising lightly or moderately. If the accumulation in activity category A is less than 30 minutes e.g. during the previous three days or during the previous 72 hours, moderate/heavy exercise may be determined as a performance instruction. The performance instruction may also be determined on the basis of a plurality of day-specific active time accumulations. The performance instruction generator 414 may be implemented by means of a computer process to be executed in the central processing unit 106, the computer process being encoded in encoded instructions to be stored in the memory unit 108.

In an embodiment, the device 400 may comprise a game application (GAPPL) 416 whose operation depends on one or more parameters proportional to an active time accumulation. In an embodiment, the device 400 may comprise a motion detector controller 436 which receives inactive time accumulation data along with the active time accumulation data 424 and compares the inactive time accumulation with a predetermined threshold value. If the threshold value is reached, the motion detector controller 436, through a mode shift command 438, shifts the motion detector 402 to a measurement mode wherein motion data is generated discontinuously at predetermined time intervals.

Figure 5:
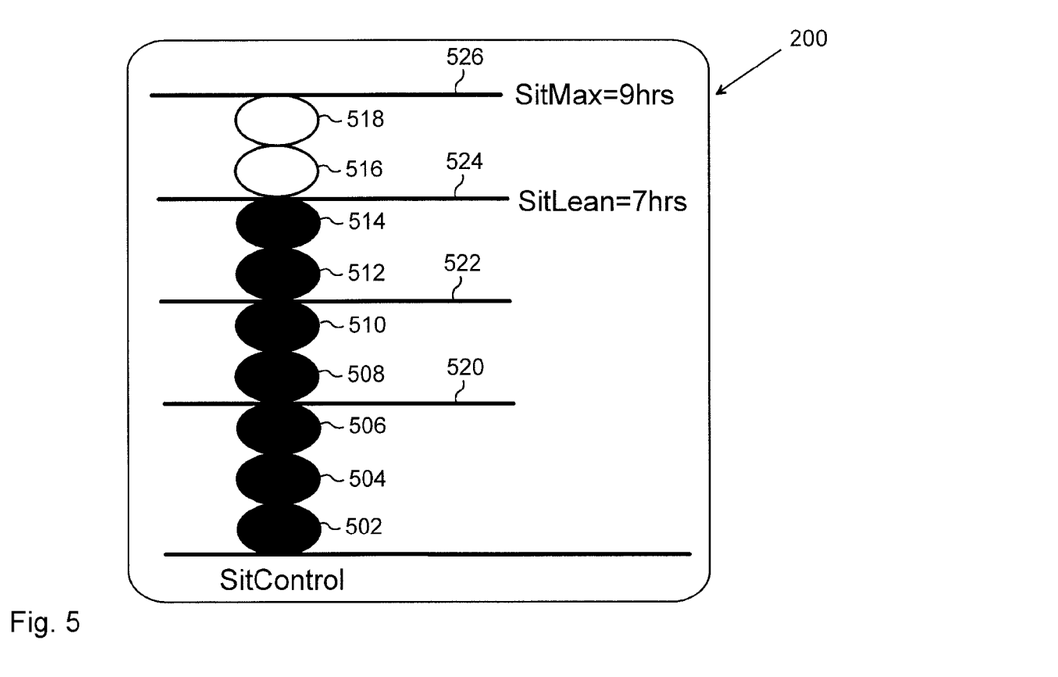
FIG. 5 shows an example of a user interface according to an embodiment.

FIG. 5 shows an example of a user interface 500 of an electronic device. In this example, a user inactivity level is indicated to the user in the form of a graphical representation.

In the example of FIG. 5, the user inactivity level is indicated by means of a SitControl function. The inactivity level is determined e.g. on the basis of inactive time spent by the user sitting and in a non-active manner. The amount of accumulated inactive time as well as certain predetermined threshold values are indicated to the user visually and digitally to enable the accumulated inactive time to be compared with the threshold values visually. Furthermore, the device may indicate reaching each threshold value separately e.g. by means of audible signals, vibration, or visually.

In FIG. 5, ovals 502, 504, 506, 508, 510, 512, 514, 516, 518 located on top of one another each describe an hour's time. Black ovals 502, 504, 506, 508, 510, 512, 514 illustrate one-hour time periods accumulated as a result of an activity, e.g. sitting, within the limits of an inactivity level. The graphic representation may include any symbols, figures, and graphs or combinations thereof other than those shown in the exemplary representation of FIG. 5. In the example of FIG. 5, a SitLean threshold value 524, which, in this example, is the optimal amount of inactivity per day, has been reached. According to some research, the SitLean threshold value 524 is approximately seven hours. Remaining below this optimal threshold value 524 supports a slim and healthy build and lifestyle. The example of FIG. 5 also shows a SitMax threshold value 526, which is the maximum allowable time to be spent inactively in order to maintain or achieve a slim build. According to research, this maximum time is approximately nine hours per day. According to research, slim persons do not constantly exceed this amount.

It is also possible to determine other threshold values 520, 522, meeting which triggers various functions. For instance, reaching a particular threshold value 520, 522 may cause the device to alert the user to approach of critical threshold values 524, 526 or to the fact that the user has been inactive for a predetermined period of time.

When the user is able to concretely and visually monitor the time he or she has spent inactively, the user's awareness of his or her inactivity level and the time spent inactively increases. This may in a practical manner guide the user towards a more active lifestyle and decrease the time spent e.g. sitting.

In an embodiment, the following categories may be employed when estimating an inactivity level: over 10 hours (extremely high inactivity level), 7 to 10 hours (too high an inactivity level), 5 to 7 hours (high inactivity level), 2 to 5 hours (appropriate inactivity level), and less than 2 hours (inactivity presents no problem).

In an embodiment, the inactivity level, such as the amount of sitting, may also be monitored on a weekly basis by determining e.g. 49 hours as the allowed maximum inactive time.

Figure 6:
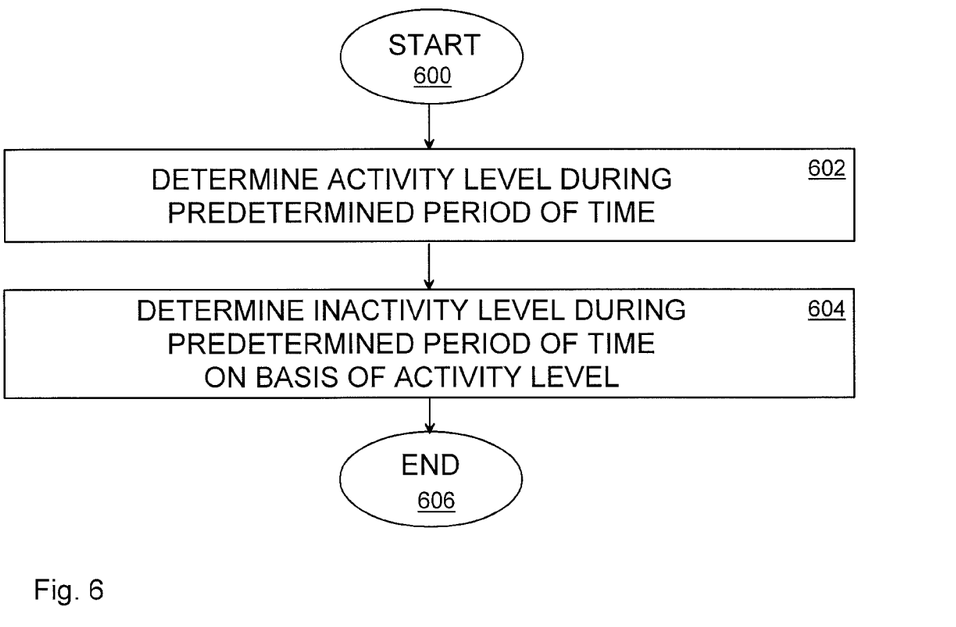
FIG. 6 shows an example of a method according to an embodiment of the invention.
Figure 7:
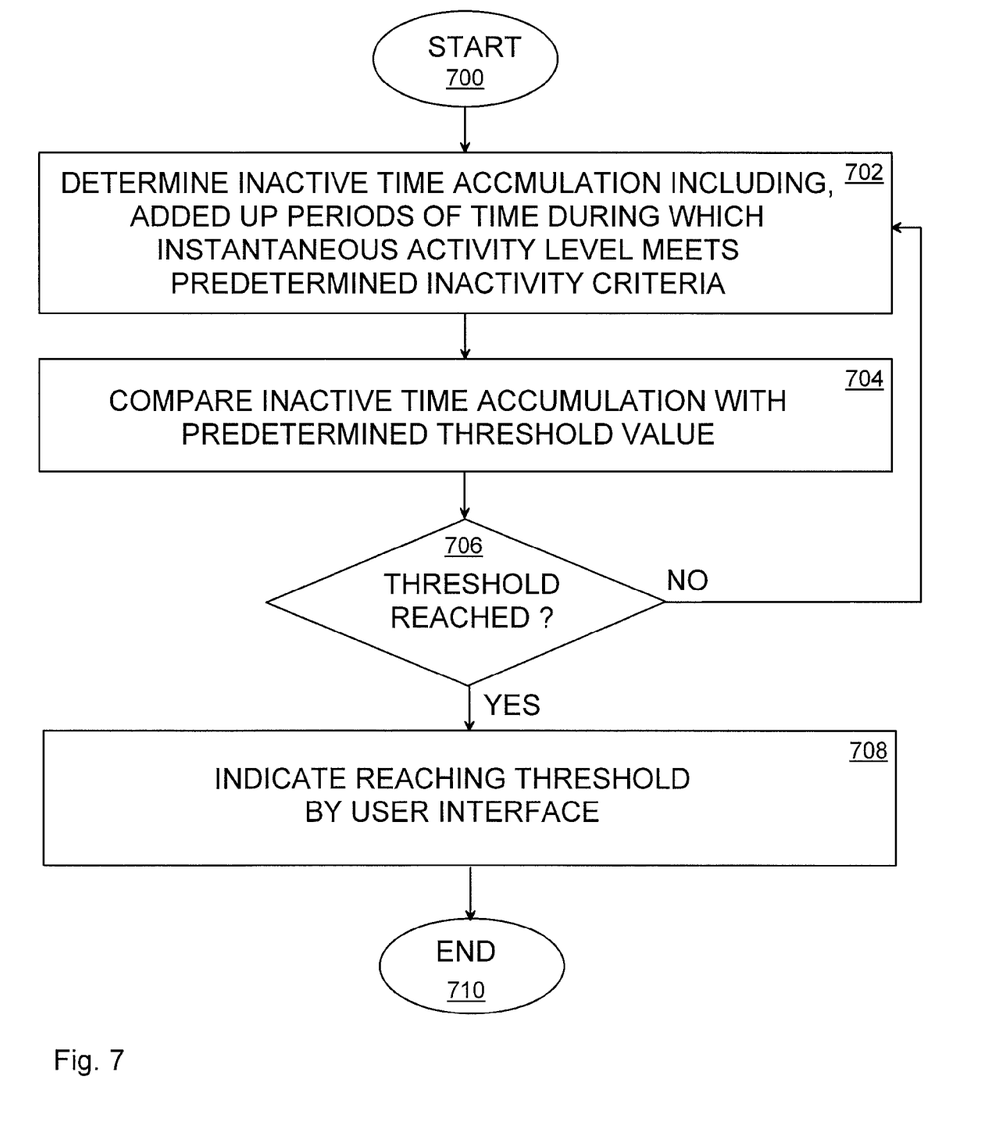
FIG. 7 shows a second example of a method according to an embodiment of the invention.

Referring to FIGS. 6 and 7, let us examine computer processes according to some embodiments of the invention, shown by means of process steps. Such process steps may also be interpreted as method steps of a method.

In 600 of FIG. 6, a computer process starts.

In 602, an activity level during a predetermined period of time is determined.

In 604, an inactivity level during a predetermined period of time is determined on the basis of the activity level.

The computer process ends in 606.

Referring to FIG. 7, a method starts in 700.

In 702, an inactive time accumulation including, added up, periods of time during which an instantaneous activity level meets predetermined inactivity criteria is determined.

In 704, the inactive time accumulation is compared with a predetermined threshold value.

In 706, a decision is made as to whether or not the threshold value has been reached.

If the threshold vales has been reached, in 708 this is indicated by means of a user interface.

In 710, the method ends.

The computer process shown in FIGS. 6 and 7 may be incorporated in a computer software product as encoded instructions which may be executed in a central processing unit 106 of a portable electronic device 100. The encoded instructions may be stored in a memory unit 108 of the portable electronic device 100.

The encoded instructions may be transferred by means of a distribution device. Such a distribution device is e.g. an electric, magnetic or optical distribution device. The distribution device may be a physical distribution device, such as a memory unit or an optical disk, or a communications signal.

Although the invention has been described above with reference to the example according to the accompanying drawings, it is apparent that the invention is not restricted thereto but may be modified in many ways within the scope of the appending claims.

What is claimed is:

1. A portable electronic device comprising:
   an active time unit for determining an activity level associated with a user of the portable electronic device during a predetermined period of time; and
   a processing unit for determining an inactivity level associated with the user of the portable electronic device during a predetermined period of time on the basis of the determined activity level, the processing unit detecting at least one of an optimal inactivity level and a maximum inactivity level, the optimal inactivity level comprising an optimal level of inactivity that is not advisable to be exceeded, the maximum inactivity level comprising a maximum level of inactivity an exceeding of which is to be avoided, the processing unit notifying the user of the portable electronic device in response to detecting at least one of the optimal inactivity level and the maximum inactivity level, thereby increasing the user's awareness of the user's inactivity level and increasing the user's ability to maintain a more active lifestyle.

2. A portable electronic device as claimed in claim 1, wherein in order to determine the user activity level, the active time unit is configured to add up periods of time during which an instantaneous motion intensity value meets predetermined activity conditions.

3. A portable electronic device as claimed in claim 1, wherein the active time unit comprises at least one activity sensor for measuring the activity level associated with the user of the portable electronic device, and the processing unit is configured to use the measured activity level in determining the inactivity level.

4. A portable electronic device as claimed in claim 3, wherein at least one activity sensor is configured to measure muscular activity of the user of the portable electronic device.

5. A portable electronic device as claimed in claim 3, wherein at least one activity sensor is configured to measure heart rate of the user of the portable electronic device.

6. A portable electronic device as claimed in claim 1, wherein the active time unit comprises at least one acceleration sensor for measuring acceleration from movement of the device when the user of the portable electronic device is moving, and the processing unit is configured to use the measured acceleration in determining the inactivity level.

7. A portable electronic device as claimed in claim 1, wherein the processing unit is configured to detect reaching at least one predetermined threshold value in the determined inactivity level.

8. A portable electronic device as claimed in claim 7, wherein the detected predetermined threshold value is the optimal inactivity level during the predetermined period of time.

9. A portable electronic device as claimed in claim 7, wherein the detected predetermined threshold value is the maximum inactivity level during the predetermined period of time.

10. A portable electronic device as claimed in claim 1, wherein the device further comprises an indicator for indicating the determined inactivity level.

11. A portable electronic device as claimed in claim 10, wherein the indicator is configured to indicate reaching at least one predetermined threshold level in the inactivity level.

12. A portable electronic device as claimed in claim 1, wherein the portable electronic device comprises a wrist device.

13. A method comprising:
determining an activity level associated with the user of a portable electronic device during a predetermined period of time on the basis of the portable electronic device used by the user;
determining an inactivity level associated with the user of the portable electronic device during the predetermined period of time on the basis of the determined activity level;
detecting at least one of the optimal inactivity level and a maximum inactivity level, the optimal inactivity level comprising an optimal level of inactivity that is not advisable to be exceeded, the maximum inactivity level comprising a maximum level of inactivity an exceeding of which is to be avoided; and
notifying the user of the portable electronic device in response to detecting at least one of the optimal inactivity level and the maximum inactivity level, thereby increasing the user's awareness of the user's inactivity level and increasing the user's ability to maintain a more active lifestyle.

14. A method as claimed in claim 13, comprising, in order to determine the activity level associated with the user of the portable electronic device, adding up periods of time during which an instantaneous motion intensity value meets predetermined activity conditions.

15. A method as claimed in claim 13, comprising measuring the activity level associated with the user of the portable electronic device by means of at least one activity sensor, and using the measured activity level in determining the inactivity level.

16. A method as claimed in claim 15, comprising measuring muscular activity of the user of the portable electronic device by means of at least one activity sensor.

17. A method as claimed in claim 15, comprising measuring heart rate of the user of the portable electronic device by means of at least one activity sensor.

18. A method as claimed in claim 13, comprising measuring acceleration from movement of the device when the user of the portable electronic device is moving by means of at least one acceleration sensor, and using the measured acceleration in determining the inactivity level.

19. A method as claimed in claim 13, comprising detecting reaching at least one predetermined threshold value in the determined inactivity level.

20. A method as claimed in claim 19, comprising the detected predetermined threshold value being the optimal inactivity level during the predetermined period of time.

21. A method as claimed in claim 19, comprising the detected predetermined threshold value being the maximum inactivity level during the predetermined period of time.

22. A method as claimed in claim 13, comprising indicating the determined inactivity level.

23. A method as claimed in claim 22, comprising indicating reaching at least one predetermined threshold value in the inactivity level.

24. A computer-readable medium comprising instructions that, when executed by a processing device, cause the processing device to:
determine an activity level associated with the user of a portable electronic device during a predetermined period of time on the basis of data produced by the portable electronic device used by the user;
determine an inactivity level associated with the user of the portable electronic device during the predetermined period of time on the basis of the determined activity level;
detect at least one of an optimal inactivity level and a maximum inactivity level, the optimal inactivity level comprising an optimal level of inactivity that is not advisable to be exceeded, the maximum inactivity level comprising a maximum level of inactivity an exceeding of which is to be avoided; and
notify the user of the portable electronic device in response to detecting at least one of the optimal inactivity level and the maximum inactivity level, thereby increasing the user's awareness of the user's inactivity level and increasing the user's ability to maintain a more active lifestyle.

25. A computer-readable medium as claimed in claim 24, wherein the instructions, when executed by the processing device, further cause the processing device to add up periods of time during which an instantaneous motion intensity value meets predetermined activity conditions.

26. A computer-readable medium as claimed in claim 24, wherein the instructions, when executed by the processing device, further cause the processing device to measure the activity level associated with the user of the portable electronic device by means of at least one activity sensor, and using the measured activity level in determining the inactivity level.

27. A computer-readable medium as claimed in claim 24, wherein the instructions, when executed by the processing device, further cause the processing device to measure acceleration from movement of the device when the user of the portable electronic device is moving by means of at least one acceleration sensor, and using the measured acceleration in determining the inactivity level.

28. A computer-readable medium as claimed in claim 24, wherein the instructions, when executed by the processing device, further cause the processing device to detect reaching at least one predetermined threshold value in the determined inactivity level.

29. A computer-readable medium as claimed in claim 24, wherein the instructions, when executed by the processing device, further cause the processing device to indicate the determined inactivity level.

30. A computer-readable medium as claimed in claim 29, wherein the instructions, when executed by the processing device, further cause the processing device to indicate reaching at least one predetermined threshold value in the inactivity level.

* * * * *